United States Patent [19]

Welter

[11] Patent Number: 5,087,288
[45] Date of Patent: Feb. 11, 1992

[54] HERBICIDAL THIOPARACONIC ACID DERIVATIVES

[75] Inventor: Thomas R. Welter, Webster, N.Y.

[73] Assignee: Eastman Kodak Company, Rochester, N.Y.

[21] Appl. No.: 583,537

[22] Filed: Sep. 17, 1990

[51] Int. Cl.$^5$ .................... A01n 43/10; C07D 333/32
[52] U.S. Cl. ........................................ 71/90; 549/28; 549/60; 549/61; 549/62; 549/64; 546/212; 548/192; 548/212; 548/236; 548/245; 548/362; 548/327; 544/379
[58] Field of Search ............... 71/90; 549/60, 61, 28, 549/62, 64; 514/445; 546/212; 548/192, 212, 236, 245, 362; 544/379; 548/527

[56] References Cited

U.S. PATENT DOCUMENTS

| | | | |
|---|---|---|---|
| 2,976,216 | 3/1961 | DeMytt | 167/87.1 |
| 3,365,447 | 1/1968 | O'Mant | 260/240 |
| 4,599,350 | 7/1986 | Gayer et al. | 514/445 |

OTHER PUBLICATIONS

Chemical Abstracts, 35:2114 (1940).
Chemical Abstracts, 73:3433$^m$ (1970).

*Primary Examiner*—Richard L. Raymond
*Assistant Examiner*—Mark W. Russell
*Attorney, Agent, or Firm*—Judith A. Roesler

[57] ABSTRACT

A method of controlling plant growth is provided comprising applying to the plants or to a habitat thereof a herbicidally effective amount of a compound having the structure:

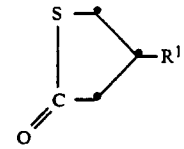

wherein
$R^1$ is selected from the group consisting of carboxy, cyano, ester

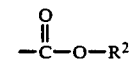

or amido

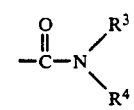

wherein
$R^2$ is selected from the group consisting of a straight-chained alkyl group or a branched-chain alkyl group, of about 1 to 8 carbon atoms,
$R^3$ and $R^4$ are selected from the group consisting of hydrogen, alkyl of about 1 to 8 carbon atoms, cycloalkyl of about 5 to 6 carbon atoms, and heterocyclyl of about 5 to 6 carbon and hetero atoms, or,
$R^3$ and $R^4$ taken together with the nitrogen atoms to which they are attached form a heterocyclyl group having 5 to 6 carbon and hetero atoms. Also, novel compounds having the above structure are provided.

9 Claims, No Drawings

HERBICIDAL THIOPARACONIC ACID DERIVATIVES

FIELD OF THE INVENTION

The present invention relates to herbicides.

BACKGROUND OF THE INVENTION

In the food agricultural industry, it is useful to provide the public with a variety of herbicides. The herbicides of this invention are derivatives of thioparaconic acid.

U.S. Pat. No. 2,976,216, filed on Nov. 4, 1959, entitled "Permanent Waving Agent", assigned to The Gillette Company, Boston, Mass., discloses a dry solid composition soluble in an aqueous medium to form a hair waving lotion comprising one molecular proportion of a member of the class consisting of thioparaconic acid and certain salts of thioparaconic acid.

Fungicidally active thiolane-2,4-dione-3-carboxamides are disclosed in U.S. Pat. No. 4,599,350, issued on July 8, 1986, entitled "Novel Thiolane-2,4-dione-3-carboxamide Fungicides", assigned to Bayer Aktiengesellschaft, Leverkusen, Fed. Rep. of Germany.

U.S. Pat. No. 3,365,447, issued on Jan. 23, 1968, entitled "2,5-Dihydro-4-hydroxy-2-oxothiophens", assigned to Imperial Chemical Industries Limited, London, England discloses thiophen derivatives which possess useful therapeutic properties.

Chemical Abstracts, 35: 2114(1940) refers to Arkiv Kemi, Mineral Geol., 14A: 22(1941) by B. Holmberg and E. Schjanberg wherein thioparaconic acid is disclosed.

Chemical Abstracts, 73: 3433$^m$(1970) refers to Mem. Fac. Eng., Kobe Univ., 197: 151(1970) by H. Akashi, R. Masuda, C. Katsuda and T. Kobayashi, wherein the reaction scheme between itaconic acid and thiourea shows the structure of thioparaconic acid as an end product.

SUMMARY OF THE INVENTION

We have developed a method of controlling plant growth which provides an alternative to existing methods.

More specifically, in accordance with the present invention, there is provided a compound having the structure:

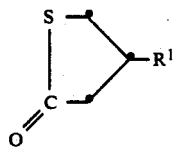

wherein $R^1$ is selected from the group consisting of cyano, ester

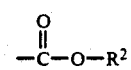

or amido

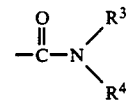

wherein $R^2$ is selected from the group consisting of a straight-chained alkyl group or a branched-chained alkyl group, of about 1 to 8 carbon atoms, $R^3$ and $R^4$ are selected from the group consisting of hydrogen, alkyl of about 1 to 8 carbon atoms, cycloalkyl of about 5 to 6 carbon atoms, and heterocyclyl of about 5 to 6 carbon and hetero atoms, or, $R^3$ and $R^4$ taken together with the nitrogen atoms to which they are attached form a heterocyclyl group having 5 to 6 carbon and hetero atoms.

In accordance with another aspect of the invention, there is provided a method of controlling plant growth comprising applying to the plants or to a habitat thereof a herbicidally effective amount of a compound having the structure:

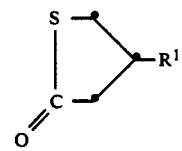

wherein $R^1$ is selected from the group consisting of carboxy, cyano, ester

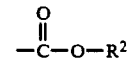

or amido

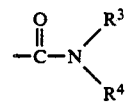

wherein $R^2$ is selected from the group consisting of a straight-chained alkyl group or a branched-chained alkyl group, of about 1 to 8 carbon atoms, $R^3$ and $R^4$ are selected from the group consisting of hydrogen, alkyl of about 1 to 8 carbon atoms, cycloalkyl of about 5 to 6 carbon atoms, and heterocyclyl of about 5 to 6 carbon and hetero atoms, or, $R^3$ and $R^4$ taken together with the nitrogen atoms to which they are attached form a heterocyclyl group having 5 to 6 carbon and hetero atoms.

It is an advantageous feature of the invention that it provides herbicidal methods which are alternatives to existing herbicidal methods.

It is also an advantageous feature of the invention that it provides novel compounds useful in herbicidal methods.

DESCRIPTION OF THE PREFERRED EMBODIMENTS

The invention provides a compound having the structure:

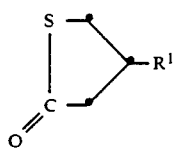

wherein
R$^1$ is selected from the group consisting of cyano, ester

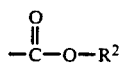

or amido

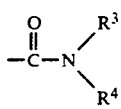

wherein
R$^2$ is selected from the group consisting of a straight-chained alkyl group or a branched-chained alkyl group, of about 1 to 8 carbon atoms, such as methyl, ethyl, propyl, butyl, pentyl, octyl, isopropyl, i-butyl, s-butyl, t-butyl, 2-ethylhexyl and isooctyl.

R$^3$ and R$^4$ are selected from the group consisting of hydrogen, alkyl of about 1 to 8 carbon atoms, such as the examples provided hereinabove, cycloalkyl of about 5 to 6 carbon atoms, such as cyclopentyl and cyclohexyl, and heterocyclyl of about 5 to 6 carbon and hetero atoms, such as furyl, thienyl, thiazolyl, oxazolyl, pyrazolyl, pyranyl, thiopyranyl, dioxanyl or, R$^3$ and R$^4$ taken together with the nitrogen atom to which they are attached form a heterocyclyl group having 5 to 6 carbon and hetero atoms, such as pyrrolidinyl, piperidinyl and piperazinyl.

Preferred compounds of the invention include esters having the above structure wherein R$^2$ is selected from the group consisting of ethyl and pentyl.

Other compounds representative of the invention include amido compounds having the above formula wherein R$^3$ and R$^4$ are selected from the group consisting of hydrogen, methyl, ethyl, propyl and butyl.

Preferred amido compounds having the above formula include those wherein R$^3$ and R$^4$ are hydrogen or methyl.

The invention also provides a method of controlling plant growth comprising applying to the plants or to a habitat thereof a herbicidally effective amount of a compound having the above structure wherein:

R$^1$ is selected from the group consisting of carboxy, cyano, ester

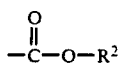

or amido

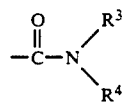

wherein
R$^2$, R$^3$ and R$^4$ are as defined above.

Preferred methods of the invention include those utilizing esters having the above formula wherein R$^2$ is selected from the group consisting of ethyl and pentyl.

Other methods representative of the invention include those utilizing amido compounds having the above formula wherein R$^3$ and R$^4$ are selected from the group consisting of hydrogen, methyl, ethyl, propyl and butyl.

Other preferred methods of the invention include those utilizing amido compounds having the above formula wherein R$^3$ and R$^4$ are hydrogen or methyl.

In general, compounds of the invention wherein R$^1$ is ester or amido as defined above are prepared according to the following reaction schemes:

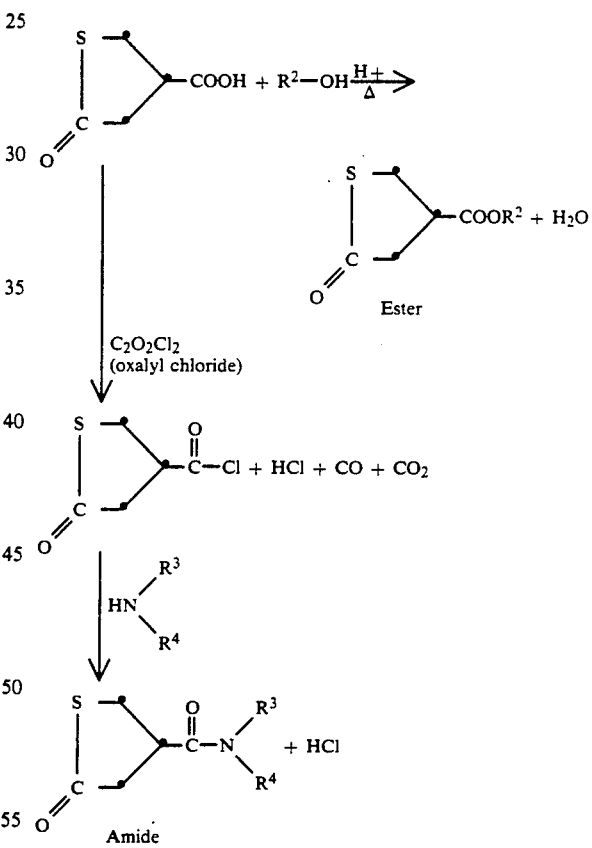

The esterification of acids with alcohols as shown above is generally described in *Advanced Organic Chemistry*, 3rd Ed., by Jerry March (1985), page 348. The acylation shown above is also generally described in *Advanced Organic Chemistry*, id at page 370. The carboxylic acid is known and can be prepared as described in Chemical Abstracts 73: 3433$^m$ (1970) discussed herein.

The preparation of compounds of the invention wherein R$^1$ is cyano as defined above are generally prepared according to the following reaction scheme:

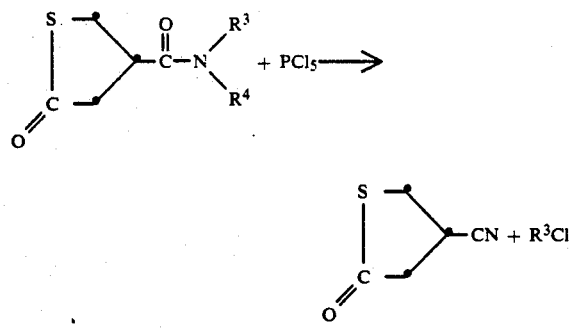

This reaction scheme is generally disclosed also in *Advanced Organic Chemistry*, id at page 933.

The cyano compound of the invention is preferably prepared according to the following reaction scheme:

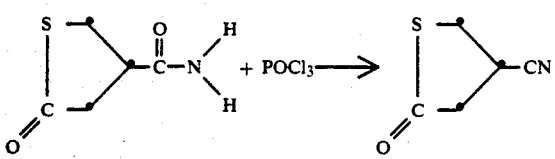

Application of the compounds which are useful in the process of the invention for purposes of herbicidal control can be accomplished employing both conventional type formulation and equipment. The compounds may, for instance, be formulated as wettable powders, dusts, dust concentrates, emulsifiable concentrates and the like which are amenable to application with conventional spraying or dusting apparatus.

For use in agriculture, the herbicides useful in this invention may be advantageously formulated as a wettable powder. Wettable powders are usually prepared by grinding and milling the ingredient with a solid carrier, such as attaclay (attapulgite) kaolin, diatomaceous earth, synthetic calcium silicate, fullers earth(calcium montmorillonite), talc, pumice, and the like. Usually, about 25% to 75% by weight of solid carrier, is used. In addition, there is generally added about 1% to 5% by weight of a dispersing agent, such as alkali metal salts of naphthalene sulfonic acid and anionic-nonionic blends, and from about 1% to 5% by weight of a surfactant, such as polyoxyethylene alcohols, acids, adducts, sorbitan fatty acid esters, sorbital esters, and the like. The amount of solid carrier is then reduced accordingly to compensate for the amount of dispersing agent(s) and surfactant(s) incorporated into the formulation.

Wettable powders are prepared in the same manner as the dust concentrates excepting that about 1% to 5% by weight of a dispersing agent such as the calcium salt of a polymerized alkyl aryl sulfonic acid, sodium lignosulfate, or sodium salt of condensed naphthalene sulfonic acid is blended with the mixture and about 1% to 5% of a surfactant, such as polyoxyethylated vegetable oil, alkyl phenoxy polyoxyethylene ethanol, sodium alkyl naphthalene sulfonate is also blended with the formulation.

Wettable powder formulations are generally prepared by admixing from about 25 percent to about 95 percent, by weight, of active ingredient with finely ground clay, such as kaolin or attapulgite, either with or without a surface active agent, emulsifier or spreader-sticker. The latter is then dispersed in water for spray application.

Wettable powders are usually dispersed in water and applied as dilute aqueous sprays at a rate of 0.28 kg to 22.4 kg/hectare of active ingredient to the area where control of undesirable plant species is desired.

In practice, the wettable powder is dispersed in water and applied as a liquid spray to the foliage of undesirable plants. Application rates should be sufficient to provide about 0.25 to 10 pounds per acre of the pyrazolium salt and, although 0.5 to 5.0 pounds per acre of said salt is generally satisfactory to control undesirable broadleaf weeds and undesirable grass plants, it should be recognized that rates exceeding 10 and as high as 20 pounds per acre can be used. These higher rates would, of course, be used in areas such as railroad sidings, beneath power lines and along hedge rows bordering property lines and fields.

Advantageously, many of the compounds useful in the process of this invention demonstrate a high degree of water solubility and lend themselves to the preparation of aqueous concentrates. Among the preferred salts are the alkali metal, ammonium or alkylammonium ones. In practice, the aqueous concentrates may be applied directly as a liquid spray to the foliage of undesirable broadleaf weeds and grassy plants. Alternatively, they may be further diluted with water and applied as dilute aqueous sprays to these undesirable plants.

The water-miscible concentrates are prepared by dissolving from 15% to 95% of the compound in 85% to 5% of a water-miscible solvent, such as water itself or another polar water-miscible solvent, such as 2-methoxyethanol, methanol, propylene glycol, diethylene glycol, diethylene glycol monoethyl ether, formamide, and dimethylformamide. Application of the material is made by adding a predetermined quantity of the water-miscible concentrate to a spray tank and applying the mixture as such or in combination with a suitable diluent, such as a further quantity of water or one of the above polar solvents.

The performance of the product in all of the above formulations, which are applied as liquid sprays, is unexpectedly improved by adding a surfactant or blend of surfactants. Conventional anionic, cationic and nonionic surfactants may be employed.

Illustrative nonionic surfactants are: alkyl polyoxyethylene ethers, polyoxethylene sorbitan monolaurate, polyoxyethylene sorbitan monoleate, alkylarylpolyglycol ethers, alkyl phenol ethoxylates, trimethyl nonyl polyethylene glycol ethers, alkyl phenol ethylene oxide condensates, octyl phenoxy polyethoxy ethanols, nonylphenyl polyethylene glycol ethers, condensates of polyoxy ethylenes, polyoxypropylenes, aliphatic polyethers, aliphatic polyesters, alkylaryl polyoxyethylene glycols, and the like.

Exemplary anionic surfactants include sodium dodecylbenzene sulfonate and the dioctyl ester of sodium sulfosuccinic acid.

Suitable cationic surfactants include dicoco dimethylammonium chloride, stearamidopropyl dimethyl betahydroxyethylammonium nitrate and the like.

These surfactants are preferably added to the spray tank at the rate of 0.1% to 5% by volume to provide good wetting of the spray solution on plant foliage.

Herbicidal concentrates containing surfactants are preferably formulated as aqueous sprays containing approximately 30% by weight of the appropriate salt, from about 25% to 50% by weight of water and the remainder of said formulation (25%-45% weight) of a selected surfactant. Surfactants which are especially useful in preparing suitable surfactant containing concentrates include an octylphenol ethylene oxide condensate, an ethanolic solution of an alkylphenol ethoxylate, a polyglycolic ether condensate produced from ethylene oxide and an alkyl phenol, and an alkyl aryl polyglycolic ether.

Dusts are generally prepared by grinding together about 1% to 25% by weight of the active agent with from about 99% to 75% by weight of a solid diluent such as kaolin, attapulgite, talc, pumice, diatomaceous earth, fullers earth (calcium montmorillonite), wood flour, or the like.

Dust concentrates are prepared in similar fashion excepting that about 25% to 95% by weight of the active agent is ground with about 75% to 5% by weight of the diluent.

Dusts and dust concentrates are similarly prepared using from about 5 percent to about 95 percent of active ingredient and from about 95 to about 5 percent of finely divided inert ingredients. These dusts are generally applied as such, or they may be further diluted with finely ground inert solids and then applied with conventional dusting apparatus.

Emulsifiable concentrates may be prepared by dissolving or dispersing the active ingredient and organic solvent, with or without emulsifying agents, surfactants or the like. Such formulations are then diluted with either water or an appropriate organic diluent prior to application.

For application of the compounds useful in the process of this invention to the foliage of the undesirable plant species, the compounds are generally formulated as postemergence herbicidal compositions by admixing a herbicidal adjuvant with a herbicidally effective amount of the compound. Suitable adjuvants include one or more conventionally solid or liquid carriers, diluents and formulation aids, particularly surfactants.

EXAMPLE I

Bioassay of Potential Herbicides—Primary Screen 7.5×7.6×6 cm units are filled with steam-sterilized soil and held in greenhouse flats (43×43×5 cm). The depth of planting and number of seeds per unit varies with each species.

Weeds tested include:

|   | Abbreviation |
|---|---|
| a. Barnyard grass (*Echinochloa crusgalli*) | BYGRASS |
| b. Green foxtail (*Setaria viridis*) | FOXTAIL |
| c. Wild oats (*Avena fatua*) | WILDOAT |
| d. Nightshade (Solanum sp.) | NSHADE |
| e. Velvetleaf (*Abutilon theophrasti*) | VLEAF |
| f. Annual morningglory (*Ipomoea purpurea*) | MGLORY |
| g. Yellow nutsedge (*Cyperus esculentus*) | YNUTSED |
| h. Pigweed (*Amaranthus retroflexus*) | PWEED |
| i. Downy brome (*Bromus teotorum*) | DBROME |

Rationale for selection of these species include:
a. Affected plants are indicators of symptomology of herbicides.
b. One or more species is sensitive to all United States commercial herbicides at the 4 pounds per acre rate.
c. Each species represents a different genus.
d. Economic importance.

e. Will germinate within 7 days and grow very well every month of the year.
f. Available source of viable seeds.

Germination tests are routinely conducted on new shipments of weeds to establish a baseline viability.

Preemergence test: Seeds are planted in a sandy loam soil mixture (3 parts sandy loam soil to 1 part perlite). Weed seeds are planted at the following densities using a volumetric measurement.

| Weed Species | No. Seeds/Pot |
|---|---|
| Barnyardgrass | 50 |
| Green foxtail | 45 |
| Wild oats | 55 |
| Nightshade | 35 |
| Velvet leaf | 20 |
| Annual Morningglory | 10 |
| Yellow nutsedge | 10 |
| Pigweed | 35 |
| Downy brome | 50 |

Postemergence test: Seeds are planted as described above except supersoil (fir bark, redwood, Canadian peat, and sand) is used. Plants are fertilized weekly with a 10:10:10 fertilizer mix.

Seedlings are thinned to the following densities:

| Weed Species | No. Seeds/Pot |
|---|---|
| Barnyardgrass | 40 |
| Green foxtail | 40 |
| Wild oats | 40 |
| Nightshade | 20 |
| Velvet leaf | 20 |
| Annual Morningglory | 5 |
| Yellow nutsedge | 5 |
| Pigweed | 10 |
| Downy brome | 4 |

The preemergence test consists of spraying the soil surface with the test compound at 4 pounds active ingredient (ai) per acre using a belt sprayer equipped with an overhead nozzle. A mixture of an octylphenoxy polyethoxy ethanol surface active agent, a polyoxyethylene sorbitan monolaurate surface active agent, and a sorbitan monolaurate surface active agent is added at 1000 ppm to increase spreadability of the compound. The compound is applied at 100 gallons per acre and 21.9 grams per square inch, and the belt speed is 0.5 miles per hour. Spraying is done within 6 hrs. after planting. The soil is watered shortly after treatment and receives daily watering of a fine mist. Little or no drainage of water out of the cup bottoms occur.

Postemergence tests involve spraying of established seedlings using the same equipment and formulation as noted above. Weeds used in postemergence studies are held in moist soil without additional watering for 48 hrs. and then receive daily watering of a fine mist spray.

A test consists of
a. Control—seed only
b. Test—seed plus compound
c. Standard

One replicate of each test is conducted. The level of control is periodically evaluated with a written evaluation at one and two weeks posttreatment.

The percentage preemergence weed control is assessed using a ranking of 0 to 4,

Post emergence evaluation:

| Ranking | |
|---|---|
| 0 | Near 100% germination, no phytotoxicity observed. |
| 1 | Near 75% seed germination, no phytotoxicity to seedlings. |
| 2 | Seed germination delayed, over 50% seed germination, and/or some phytotoxicity. |
| 3 | Less than 50% seed germination and/or extensive phytotoxicity to established plants. |
| 4 | No observed germination and/or establishment. |

| Ranking | |
|---|---|
| 0 | No chlorosis, suppression or inhibition of plant growth, etc. observed. |
| 1 | Minimal phytotoxicity, plants generally healthy. |
| 2 | Less than 50% plant injury, recovery evident. |
| 3 | Over 50% plant injury, some plant death. |
| 4 | All plants dead with no recovery. |

The test results are reported in Tables I and II.

TABLE I

Primary Results: Preemergence Herbicide Screen

| Compound | R | BYGRASS G* | BYGRASS E* | FOXTAIL G | FOXTAIL E | WILDOAT G | WILDOAT E | NSHADE G |
|---|---|---|---|---|---|---|---|---|
| | Part A | | | | | | | |
| | atrazine 4 lbs/acre | 0 | 2 | 0 | 0 | 0 | 3 | 0 |
| | simazine 2 lbs/acre | 0 | 4 | 0 | 3 | 0 | 3 | 0 |
| 1 | —OH | 2 | 2 | 2 | 2 | 2 | 2 | 1 |
| | Part B | | | | | | | |
| 2 | —OC$_2$H$_5$ | 2 | 2 | 2 | 3 | 1 | 3 | 0 |
| 3 | —O—n-C$_5$H$_{11}$ | 2 | 3 | 2 | 3 | 2 | 3 | 0 |
| 4 | —NH$_2$ | 2 | 3 | 2 | 4 | 1 | 3 | 0 |
| 5 | —NHCH$_3$ | 0 | 0 | 1 | 2 | 0 | 0 | 0 |
| 6 | —N(CH$_3$)$_2$ | 2 | 3 | 2 | 4 | 1 | 3 | 0 |
| 7 | —NH—n-C$_4$H$_9$ | 0 | 0 | 0 | 0 | 0 | 0 | 0 |
| | atrazine 4 lbs/acre | 0 | 0 | 0 | 0 | 0 | 2 | 0 |
| | simazine 4 lbs/acre | 0 | 0 | 0 | 4 | 0 | 3 | 0 |

| Compound | R | NHSADE E | V LEAF G | V LEAF E | MGLORY G | MGLORY E | YNUTSED G | YNUTSED E |
|---|---|---|---|---|---|---|---|---|
| | Part A | | | | | | | |
| | atrazine 4 lbs/acre | 4 | 0 | 4 | 0 | 4 | 0 | 0 |
| | simazine 2 lbs/acre | 4 | 0 | 4 | 0 | 3 | 0 | 0 |
| 1 | —OH | 1 | 1 | 1 | 2 | 2 | 0 | 0 |
| | Part B | | | | | | | |
| 2 | —OC$_2$H$_5$ | 0 | 0 | 0 | 1 | 3 | # | # |
| 3 | —O—n-C$_5$H$_{11}$ | 0 | 0 | 0 | 1 | 3 | 0 | 0 |
| 4 | —NH$_2$ | 0 | 0 | 0 | 1 | 3 | 0 | 0 |
| 5 | —NHCH$_3$ | 0 | 0 | 0 | 0 | 0 | 0 | 0 |
| 6 | —N(CH$_3$)$_2$ | 0 | 0 | 0 | 0 | 0 | 0 | 0 |
| 7 | —NH—n-C$_4$H$_9$ | 0 | 0 | 0 | 0 | 0 | 0 | 0 |
| | atrazine 4 lbs/acre | 0 | 0 | 0 | 0 | 3 | 0 | 0 |
| | simazine 4 lbs/acre | 3 | 0 | 0 | 0 | 4 | 0 | 0 |

| Compound | R | PWEED G | PWEED E | D BROME G | D BROME E | TOTAL** |
|---|---|---|---|---|---|---|
| | Part A | | | | | |
| | atrazine 4 lbs/acre | 3 | 4 | 0 | 4 | 25 |
| | simazine 2 lbs/acre | 0 | 2 | 0 | 4 | 27 |
| 1 | —OH | 0 | 0 | 2 | 3 | 13 |
| | Part B | | | | | |
| 2 | —OC$_2$H$_5$ | 1 | 2 | 1 | 3 | 16 |
| 3 | —O—n-C$_5$H$_{11}$ | 0 | 2 | 2 | 3 | 17 |
| 4 | —NH$_2$ | # | # | 2 | 3 | 16 |
| 5 | —NHCH$_3$ | 0 | 0 | 0 | 1 | 3 |
| 6 | —N(CH$_3$)$_2$ | 0 | 0 | 0 | 0 | 10 |
| 7 | —NH—n-C$_4$H$_9$ | 0 | 4 | 1 | 0 | 4 |
| | atrazine 4 lbs/acre | 0 | 4 | 0 | 2 | 11 |

TABLE I-continued

Primary Results: Preemergence Herbicide Screen

| | | | | | |
|---|---|---|---|---|---|
| simazine 4 lbs/acre | 0 | 4 | 0 | 3 | 21 |

*G - Germinate;
E = Emergence
**The totals are of the "emergence" data only, which is more meaningful
No germination

TABLE II

Primary Results: Postemergence Herbicide Screen

Structure: $S{-}C({=}O){-}R$ on a cyclic ketone

| Compound | R | BYGRASS 1 | BYGRASS 2* | FOXTAIL 1 | FOXTAIL 2 | WILDOAT 1 | WILDOAT 2 | NSHADE 1 | NHSADE 2 | V LEAF 1 | V LEAF 2 | MGLORY 1 | MGLORY 2 | YNUTSED 1 | YNUTSED 2 | PWEED 1 | PWEED 2 | D BROME 1 | D BROME 2 | TOTAL*** |
|---|---|---|---|---|---|---|---|---|---|---|---|---|---|---|---|---|---|---|---|---|
| Part A | | | | | | | | | | | | | | | | | | | | |
| | atrazine 4 lbs/acre | 2 | 1 | 1 | 1 | 2 | 2 | 3 | 4 | 3 | 3 | 3 | 4 | 1 | 1 | 3 | 4 | 2 | 3 | 23 |
| | simazine 2 lbs/acre | 2 | 1 | 2 | 2 | 2 | 2 | 3 | 3 | 1 | 1 | 2 | 3 | 0 | 0 | 3 | 4 | 3 | 3 | 19 |
| 1 | —OH | 2 | 2 | 2 | 2 | 2 | 1 | 2 | 2 | 2 | 1 | 2 | 2 | 2 | 2 | 2 | 2 | 3 | 3 | 17 |
| Part B | | | | | | | | | | | | | | | | | | | | |
| 2 | —OC$_2$H$_5$ | 1 | 3 | 2 | 3 | 2 | 3 | 1 | 1 | 1 | 1 | 1 | 1 | 1 | 2 | 1 | 3 | 2 | 3 | 20 |
| 3 | —O—n-C$_5$H$_{11}$ | 2 | 3 | 2 | 3 | 2 | 3 | 2 | 3 | 2 | 2 | 2 | 3 | 1 | 2 | 2 | 3 | 3 | 3 | 25 |
| 4 | —NH$_2$ | 0 | 0 | 0 | 0 | 0 | 0 | 1 | 1 | 0 | 0 | 0 | 1 | 0 | 0 | 0 | 0 | 1 | 1 | 3 |
| 5 | —NHCH$_3$ | 0 | 0 | 1 | 1 | 1 | 1 | 0 | 0 | 0 | 0 | 0 | 1 | 0 | 0 | 0 | 0 | 1 | 1 | 4 |
| 6 | —N(CH$_3$)$_2$ | 0 | 0 | 0 | 0 | 0 | 0 | 1 | 1 | 0 | 0 | 0 | 0 | 0 | 0 | 0 | 0 | 0 | 1 | 2 |
| 7 | —NH—n-C$_4$H$_9$ | 1 | 1 | 1 | 3 | 1 | 1 | 0 | 0 | 0 | 0 | 0 | 0 | 0 | 0 | 0 | 1 | 2 | 2 | 8 |
| | atrazine 4 lbs/acre | 1 | 3 | 1 | 3 | 1 | 2 | 1 | 4 | 1 | 4 | 3 | 3 | 0 | 1 | 3 | 4 | 1 | 4 | 28 |
| | simazine 2 lbs/acre | 1 | 4 | 1 | 3 | 1 | 2 | 2 | 4 | 1 | 4 | 2 | 3 | 0 | 1 | 1 | 4 | 0 | 3 | 28 |

1 = 1st week;
2 = 2nd week emergence
**The totals are of the 2nd week data only, which is more meaningful

EXAMPLE II

Preparation of N-n-Butylthioparaconic Acid Amide

A mixture of thioparaconic acid (2.19 g, 15.0 mmol), oxalyl chloride (2.0 mL, 23 mmol) and dimethylformamide (3 drops) in dichloromethane (50 mL) was stirred at ambient temperature until gas evolution substantially showed. An additional portion of oxalyl chloride was added (0.4 mL, 5 mmol), and when gas evolution again ceased, the mixture was concentrated in vacuo. Twice, portions of cyclohexane (50 mL) were added and similarly evaporated. The residue was dissolved in tetrahydrofuran (50 mL), the solution chilled, and n-butylamine (3.0 mL, 30 mmol) added. The mixture was stirred thirty minutes. It was then poured into water. Ethyl acetate extractive workup gave a crude solid. Recrystallization from t-butyl methyl ether afforded N-butylthioparaconic acid amide as a cream solid (1.19 g, 39.4%), mp 63°–64° C. Structural assignment was based upon $^1$H NMR spectroscopic analysis.

Other, thioparaconic acid amides were prepared in a similar manner. Structural assignments were based upon $^1$H NMR spectroscopic analysis. The resulting thioparaconic acid amides are shown in Table III.

EXAMPLE III

Preparation of Ethyl Thioparaconate

A mixture of thioparaconic acid (14.6 g, 0.100 mmol) ethanol (25 mils), benzene (100 mL) and concentrated sulfuric acid (2 mL) was heated at reflux overnight in apparatus having a water trap to allow removal of water. The mixture was then concentrated in vacuo. The residue was distilled bulb-to-bulb at 0.1 torr, 120° C. to provide ethyl thioparaconate as a colorless oil (15.3 g, 87.9%). The $^1$H NMR spectrum was consistent with the assigned structure.

EXAMPLE IV

Preparation of n-Pentyl Thioparaconic Acid

In a similar fashion, n-pentyl thioparaconate was prepared and purified by distillation, bulb-to-bulb at 0.1 torr, 130° C. The $^1$H NMR spectrum was consistent with the assigned structure.

TABLE III

Thioparaconic Acid Amides

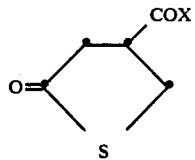

| Example | X | Recrystallization Solvent | Melting Point °C. |
|---|---|---|---|
| V | NH$_2$ | Ethanol | 151–152 |
| VI | NHCH$_3$ | n-Butyl methyl ether | 94–95 |
| VII | N(CH$_3$)$_2$ | Toluene | 67–69 |

The invention has been described in detail with particular reference to certain preferred embodiments thereof, but it will be understood that variations and modifications can be effected within the spirit and scope of the invention.

What is claimed is:

1. A compound having the structure:

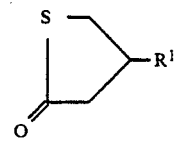

wherein
R$^1$ is carboxy cyano, ester

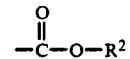

or amido

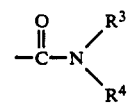

wherein
R$^2$ is a straight-chained alkyl group or a branched-chain alkyl group having 1 to 8 carbon atoms, and
R$^3$ and R$^4$ independently of one another represent hydrogen, an alkyl having 1 to 8 carbon atoms, a cycloalkyl having 5 to 6 carbon atoms, or a heterocyclyl having 5 to 6 carbon and hetero atoms, with said hetero atoms selected from sulfur, nitrogen, and oxygen, or,
R$^3$ and R$^4$ taken together with the nitrogen atom of said amido group represent pyrrolidinyl, piperidinyl, or piperazinyl.

2. The compound according to claim 1 wherein R$^2$ is ethyl or pentyl.

3. The compound according to claim 1 wherein R$^3$ and R$^4$ independently of one another represent hydrogen, methyl, ethyl, propyl or butyl.

4. The compound according to claim 1 wherein R$^3$ and R$^4$ independently of one another represent hydrogen or methyl.

5. A method of controlling plant growth comprising applying to the plants or to a habitat thereof a herbicidally effective amount of a compound having the structure:

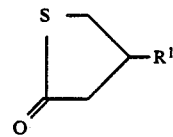

wherein
R$^1$ is carboxy, cyano, ester

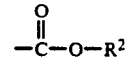

or amido

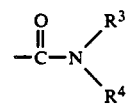

wherein $R^2$ is of straight-chained alkyl group or a branched-chain alkyl group having 1 to 8 carbon atoms, $R^3$ and $R^4$ independently of one another represent hydrogen, an alkyl having 1 to 8 carbon atoms, a cycloalkyl having 5 to 6 carbon atoms, or a heterocyclyl having 5 to 6 carbon and hetero atoms, with said hetero atoms selected from sulfur, nitrogen, and oxygen, or $R^3$ and $R^4$ taken together with the nitrogen atoms of said amido group represent pyrrolidinyl, piperidinyl, or piperazinyl.

6. A method according to claim 5 wherein $R^2$ is ethyl or pentyl.

7. A method according to claim 5 wherein $R^3$ and $R^4$ independently of one another represent hydrogen, methyl, ethyl, propyl or butyl.

8. A method according to claim 5 wherein $R^3$ and $R^4$ independently of one another represent hydrogen or methyl.

9. A herbicidal composition which contains a carrier, and, as an active ingredient, an effective amount of the compound according to claim 1.

* * * * *

UNITED STATES PATENT AND TRADEMARK OFFICE
CERTIFICATE OF CORRECTION

PATENT NO. : 5,087,288
DATED : February 11, 1992
INVENTOR(S) : Thomas R. Welter

It is certified that error appears in the above-identified patent and that said Letters Patent is hereby corrected as shown below:

Column 14, line 10 should read: $--R^1$ is cyano, ester--,

Signed and Sealed this

Fourth Day of May, 1993

Attest:

MICHAEL K. KIRK

Attesting Officer    Acting Commissioner of Patents and Trademarks